(12) United States Patent
Biedermann et al.

(10) Patent No.: US 9,101,403 B2
(45) Date of Patent: Aug. 11, 2015

(54) BONE ANCHORING ELEMENT AND STABILIZATION DEVICE FOR BONES, IN PARTICULAR FOR THE SPINAL COLUMN

(75) Inventors: Lutz Biedermann, VS-Villingen (DE); Jürgen Harms, Karlsruhe (DE); Helmar Rapp, Deißlingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 942 days.

(21) Appl. No.: 12/550,654

(22) Filed: Aug. 31, 2009

(65) Prior Publication Data

US 2010/0094348 A1 Apr. 15, 2010

Related U.S. Application Data

(60) Provisional application No. 61/094,664, filed on Sep. 5, 2008.

(30) Foreign Application Priority Data

Sep. 5, 2008 (EP) ..................................... 08015721

(51) Int. Cl.
    *A61B 17/70* (2006.01)
(52) U.S. Cl.
    CPC ........... *A61B 17/7037* (2013.01); *A61B 17/701* (2013.01); *A61B 17/7011* (2013.01); *A61B 17/7028* (2013.01); *A61B 17/7032* (2013.01); *A61B 17/7041* (2013.01)

(58) Field of Classification Search
    CPC ................... A61B 17/70–17/7008; A61B 17/7019–17/7034; A61B 17/8605
    USPC ................... 606/300–321, 246–279
    See application file for complete search history.

(56) References Cited

U.S. PATENT DOCUMENTS

| | | | |
|---|---|---|---|
| 4,697,582 A | 10/1987 | William | |
| 5,611,801 A * | 3/1997 | Songer | 606/308 |
| 5,702,395 A * | 12/1997 | Hopf | 606/250 |
| 5,800,435 A * | 9/1998 | Errico et al. | 606/261 |
| 5,863,293 A * | 1/1999 | Richelsoph | 606/278 |
| 6,086,590 A * | 7/2000 | Margulies et al. | 606/263 |

(Continued)

FOREIGN PATENT DOCUMENTS

| | | |
|---|---|---|
| CA | 2 577 436 A1 | 6/2006 |
| DE | 101 17 426 A1 | 10/2002 |

(Continued)

OTHER PUBLICATIONS

European Search Report dated Nov. 20, 2008 for European Application No. 08015721.7, Applicant Biedermann Motech GmbH, European Search Report mailed Dec. 9, 2008 (9 pgs.).

*Primary Examiner* — Eduardo C Robert
*Assistant Examiner* — Michelle C Eckman
(74) *Attorney, Agent, or Firm* — Christie, Parker & Hale, LLP

(57) ABSTRACT

A bone anchoring element includes an anchoring section for anchoring in the bone and a receiving part connected to the anchoring section. The receiving part includes an opening suitable for accommodation of a stabilization rod having a rod axis, the opening being limited along the rod axis by two side walls. The side walls include guides orientated along the rod axis for guiding at least one connection rod therethrough.

36 Claims, 9 Drawing Sheets

(56) References Cited

U.S. PATENT DOCUMENTS

| | | | |
|---|---|---|---|
| 6,645,207 B2 * | 11/2003 | Dixon et al. | 606/261 |
| 6,706,044 B2 * | 3/2004 | Kuslich et al. | 606/261 |
| 7,166,109 B2 * | 1/2007 | Biedermann et al. | 606/279 |
| 7,588,588 B2 * | 9/2009 | Spitler et al. | 606/246 |
| 7,717,941 B2 * | 5/2010 | Petit | 606/257 |
| 2002/0055740 A1 * | 5/2002 | Lieberman | 606/61 |
| 2003/0144664 A1 | 7/2003 | Cavagna et al. | |
| 2004/0039388 A1 * | 2/2004 | Biedermann et al. | 606/71 |
| 2004/0111088 A1 | 6/2004 | Picetti et al. | |
| 2004/0181224 A1 * | 9/2004 | Biedermann et al. | 606/61 |
| 2004/0249378 A1 * | 12/2004 | Saint Martin et al. | 606/61 |
| 2005/0085815 A1 | 4/2005 | Harms et al. | |
| 2005/0171537 A1 | 8/2005 | Mazel et al. | |
| 2005/0228378 A1 * | 10/2005 | Kalfas et al. | 606/61 |
| 2006/0089644 A1 * | 4/2006 | Felix | 606/61 |
| 2006/0142758 A1 | 6/2006 | Petit | |
| 2007/0049937 A1 | 3/2007 | Matthis et al. | |
| 2007/0225708 A1 * | 9/2007 | Biedermann et al. | 606/61 |
| 2007/0233073 A1 | 10/2007 | Wisnewski et al. | |
| 2007/0288008 A1 * | 12/2007 | Park | 606/61 |
| 2008/0058818 A1 * | 3/2008 | Schwab | 606/73 |
| 2008/0177328 A1 * | 7/2008 | Perez-Cruet et al. | 606/279 |
| 2008/0177335 A1 * | 7/2008 | Melkent | 606/309 |
| 2008/0262546 A1 | 10/2008 | Calvosa et al. | |
| 2008/0262551 A1 * | 10/2008 | Rice et al. | 606/268 |
| 2008/0262553 A1 * | 10/2008 | Hawkins et al. | 606/278 |
| 2008/0269810 A1 * | 10/2008 | Zhang et al. | 606/305 |
| 2009/0131982 A1 * | 5/2009 | Schwab | 606/246 |
| 2010/0087865 A1 * | 4/2010 | Biedermann et al. | 606/264 |

FOREIGN PATENT DOCUMENTS

| | | |
|---|---|---|
| EP | 1 795 134 A1 | 6/2007 |
| EP | 1 810 624 A1 | 7/2007 |
| EP | 1 891 904 A1 | 2/2008 |
| EP | 1 923 011 A1 | 5/2008 |
| WO | WO 03/034930 A1 | 5/2003 |
| WO | WO 2004/105577 A2 | 12/2004 |
| WO | WO 2006/066685 A1 | 6/2006 |
| WO | WO 2007/038429 A1 | 4/2007 |
| WO | WO 2007/060534 A2 | 5/2007 |

* cited by examiner

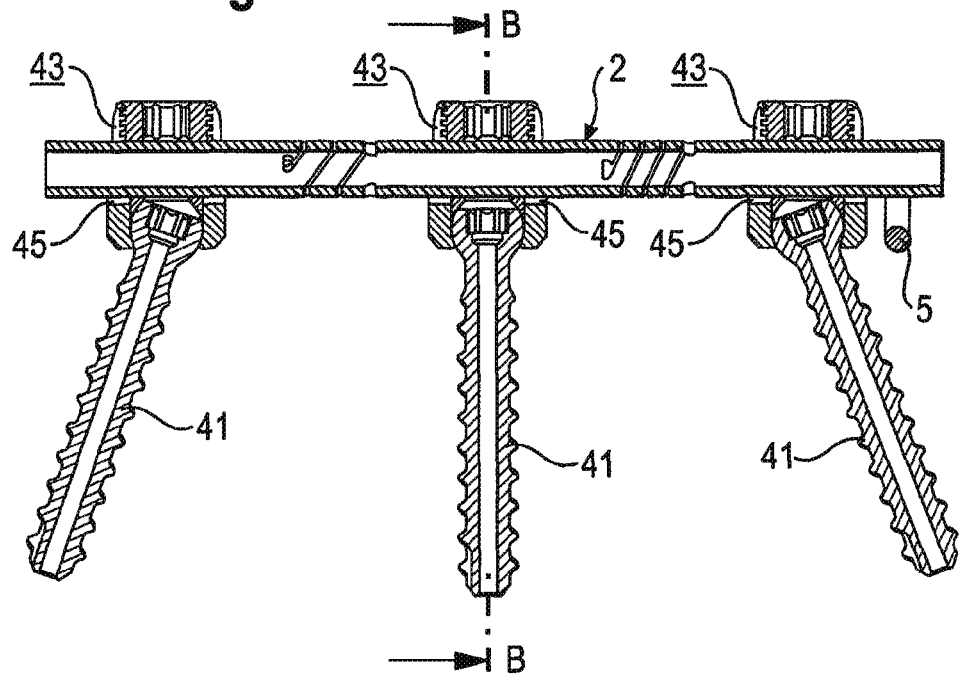
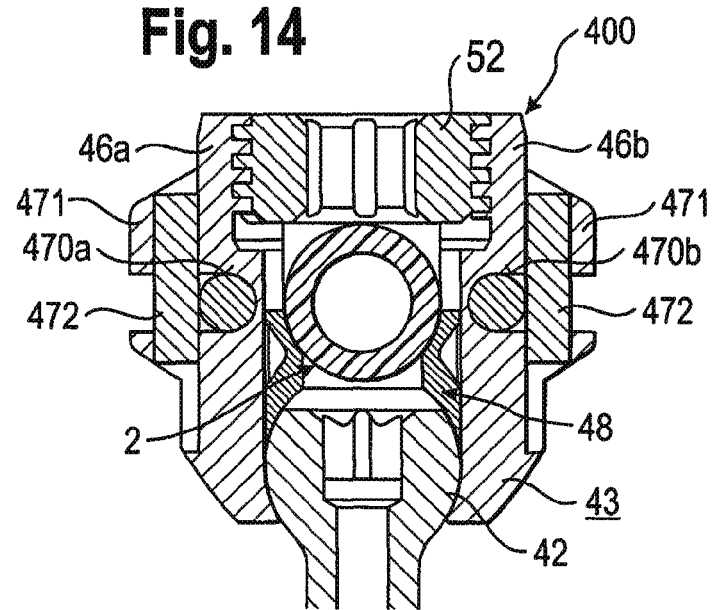

BONE ANCHORING ELEMENT AND STABILIZATION DEVICE FOR BONES, IN PARTICULAR FOR THE SPINAL COLUMN

CROSS-REFERENCE TO RELATED APPLICATION(S)

The present application claims the benefit of U.S. Provisional Patent Application Ser. No. 61/094,664, filed Sep. 5, 2008, the contents of which are hereby incorporated by reference in their entirety, and claims priority from European Patent Application EP 08 015 721.7, filed Sep. 5, 2008, the contents of which are hereby incorporated by reference in their entirety.

BACKGROUND

The present application relates to a bone anchoring element and to a stabilization device for bones, in particular for the spinal column, including such a bone anchoring element.

In the case of replacement of a severely injured or degenerated intervertebral disc or vertebra by fusion cages or bone segments stabilization devices using rigid metal rods are commonly used which are anchored in the neighboring vertebrae by polyaxial bone screws.

In specific clinical applications it is advantageous to maintain a certain mobility of the motion segments of the spinal column. In these cases, a dynamic stabilization system having bone anchoring elements and flexible rods are used. For example, US 2005/0085815 A1 and US 2007/0049937 A1 describe dynamic stabilization systems having a hollow metallic rod with a flexible section formed by a helix-shaped recess in the wall and a core provided in the hollow rod.

A dynamic stabilization device using polyaxial screws and an elastomer rod is described in EP 1 795 134 A1.

The known stabilization devices with flexible rods are suitable for the dynamic stabilization and motion control of the spinal column with respect to axial tension and compression forces.

Due to the anatomy of the spinal column, small sized implant constructs are required. Therefore, the flexible rods should have small outer diameters which makes it possible to design the receiving part of the polyaxial screw with a low profile and small overall dimensions.

In clinical cases of early degeneration or partial damages or injuries of intervertebral discs, the corresponding motion segments of the spinal column are subject to increased rotational movements and/or increased shearing forces. Such rotational movements and shearing and/or bending forces can cause strong pain. In addition, the flexible rods made of metal or elastomers may not be able to withstand higher forces for a long time due to their small diameter. In particular, shearing and rotational forces may cause an overload of the flexible rod.

Based on the foregoing, there is a need to provide a bone anchoring element and a stabilization device, in particular for the spinal column, which is suitable for cases in which increased rotational and shearing movements of the spinal column are present.

SUMMARY

A disclosed bone anchoring element includes a receiving part having a U-shaped recess forming a channel in which a stabilizing rod can be inserted and additionally includes lateral guides for accommodating connection rods with a smaller diameter. A disclosed stabilization device includes at least two such bone anchoring elements and at least one connection rod. The bone anchoring element is preferably a polyaxial bone screw.

The bone anchoring element and the stabilization device has an increased resistance against shearing and rotational forces without hindering the axial damping and the precision adjustment of the stabilization device and it offers a modular system allowing various combinations of flexible rods and connection rods.

BRIEF DESCRIPTION OF THE DRAWINGS

FIG. 13 shows a fourth embodiment of the stabilization device in a sectional view along the rod axis.

FIG. 14 shows an enlarged sectional view along line B-B of FIG. 13.

DETAILED DESCRIPTION

Figure 1:
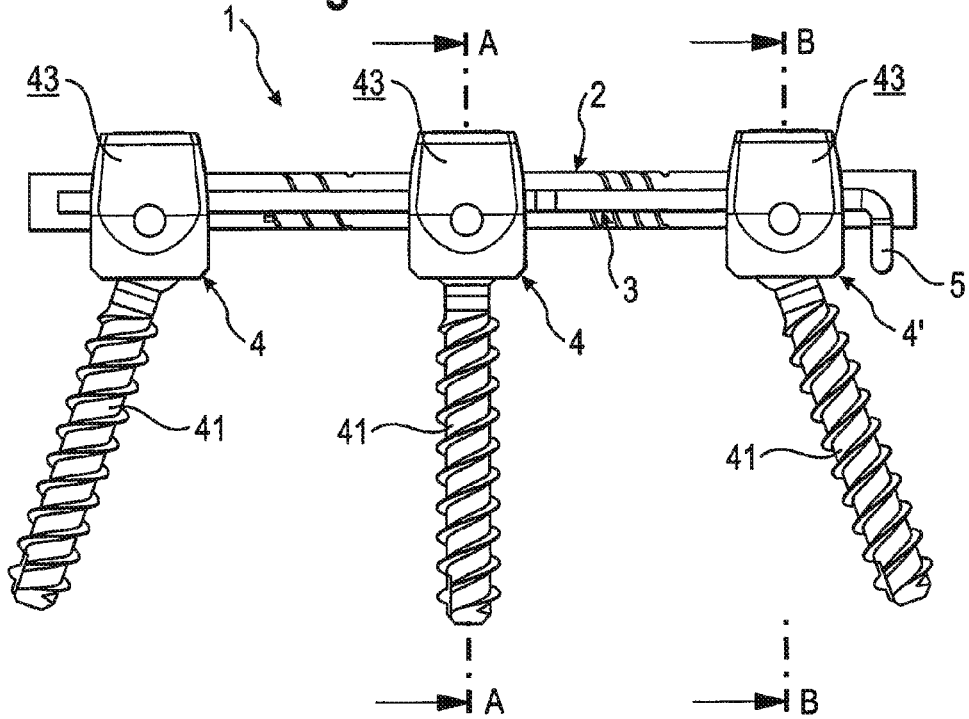
FIG. 1 shows a side view of the stabilization device according to a first embodiment.

As shown in FIGS. 1 to 5 the bone stabilization device 1 according to a first embodiment includes a flexible rod 2 and at least one laterally arranged connection rod 3 which are both connected to bone anchoring elements 4, 4'.

The flexible rod 2 includes at least a portion 2a exhibiting flexibility under the action of compression and extension forces acting along the rod axis and under the action of torsional, shearing and/or bending forces. In the embodiment shown, the flexible rod 2 is made of a hollow tube of a rigid material, such as a body compatible metal, metal alloy, in particular of titanium, Nitinol, stainless steel or of a rigid body compatible plastic material such as PEEK or carbon fiber reinforced PEEK. The length of the flexible rod is such that it spans at least the distance between two adjacent vertebrae. In the embodiment shown, the flexible rod spans the distance between three adjacent vertebrae. The flexible portion 2a is provided between rigid portions 2b. The rigid portions 2b are connected to the bone anchoring elements. The flexibility of the flexible portion is achieved by a helix-shaped recess in the wall of the hollow tube. However, any other design conferring flexibility to the rod is possible.

At both sides of the flexible rod 2 a solid connection rod 3 is arranged the diameter of which is smaller than that of the flexible rod 2. The length of each of the connection rods 3 can be the same as that of the flexible rod 2 or can be smaller than that of the flexible rod 2. In the embodiment shown, the connection rods 3 are not fully straight, but have a first straight section 3a, a step portion 3b and a second straight section 3c. The connection rods 3 are preferably less flexible when compared to the flexible section 2a of the flexible rod 2. For example, the connection rods 3 are made of a body compatible metal such as stainless steel, titanium, titanium alloys such as Nitinol or a rigid plastic material such as PEEK or carbon reinforced PEEK.

The diameter of the connections rods 3 is considerably smaller than that of the flexible stabilization rod 2. However, the diameter of the connections rods 3 has to have such a size that the connection rods 3 are rigid enough to resist bending forces.

The two lateral connection rods 3 are connected to each other at one of their respective ends by means of a bracket 5 which is formed such that it is orientated downwards or upwards in order to circumvent the flexible rod 2. The bracket 5 can be integrally formed with the rods 3 or can be a separate part which is connectable to the rods 3.

The bone anchoring element 4 is designed in the form of a polyaxial bone screw. It includes a screw element having a threaded shank 41 and spherically shaped head 42 and a receiving part 43 for receiving the flexible rod 2 and the connection rods 3. The receiving part 43 has a substantially cylindrical or cuboid shape with a first end 43a and an opposite second end 43b and a coaxial bore 44 extending from the first end 43a in the direction of the second end 43b and tapering towards the second end such that a seat is provided for the head 42 of the screw element which is pivotably held in the receiving part.

Figure 5:
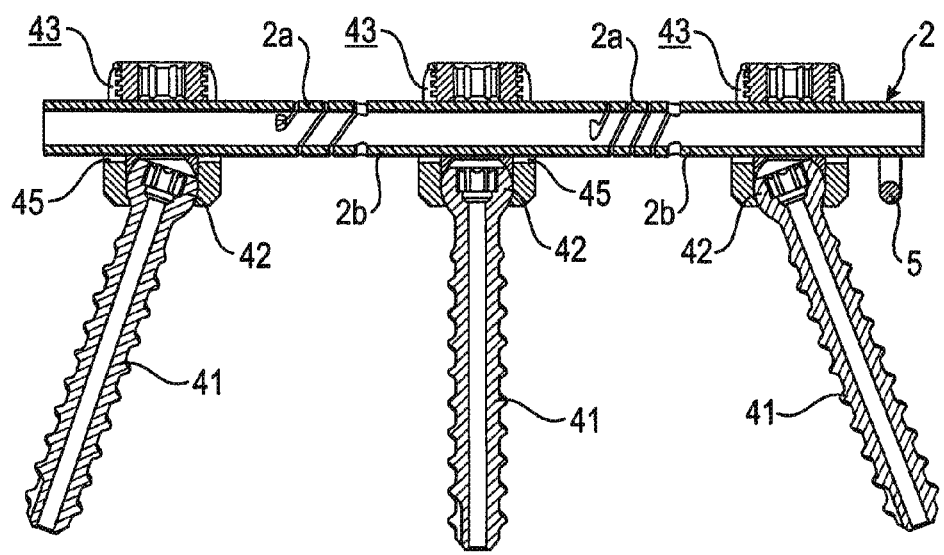
FIG. 5 shows a sectional view of the stabilization device of FIG. 4 along line C-C.
Figure 6:
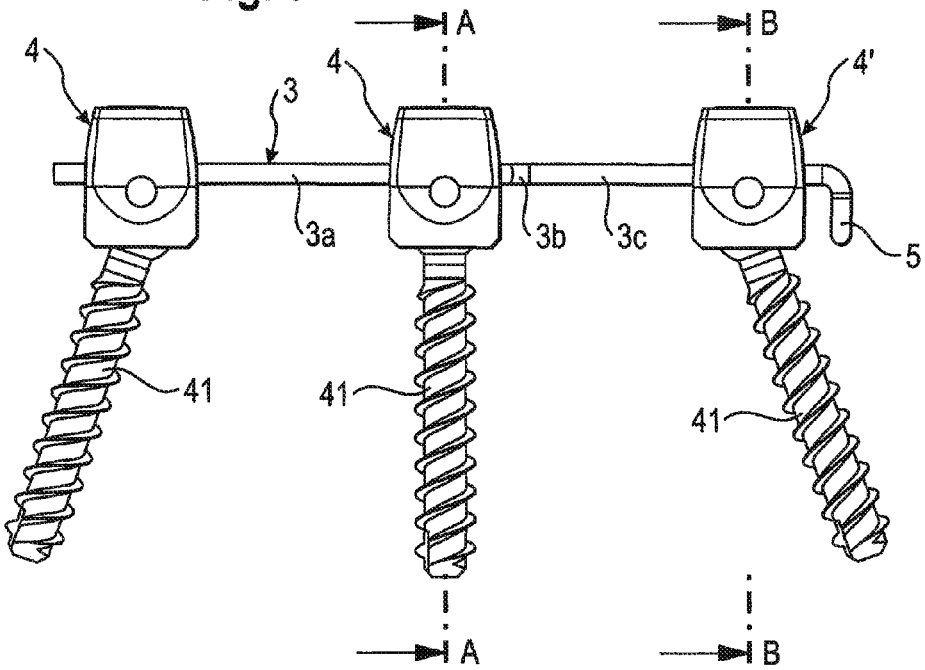
FIG. 6 shows a side view of the stabilization device according to a second embodiment.
Figure 7:
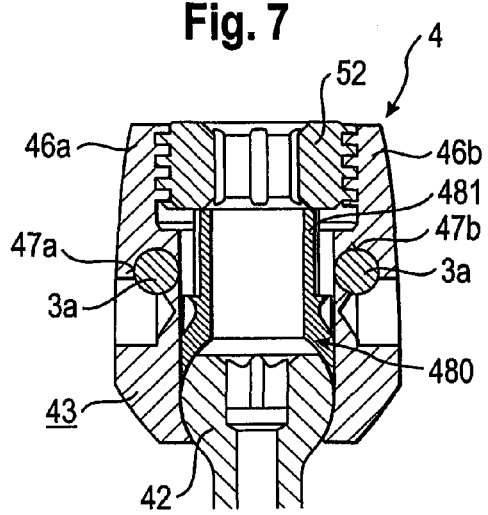
FIG. 7 shows an enlarged sectional view along line A-A of FIG. 6.
Figure 8:
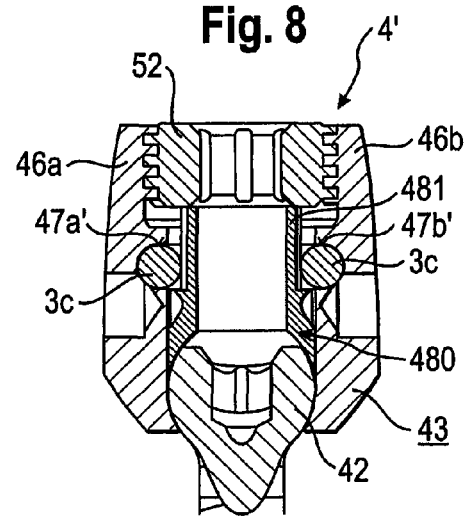
FIG. 8 shows an enlarged sectional view along line B-B of FIG. 6.
Figure 9:
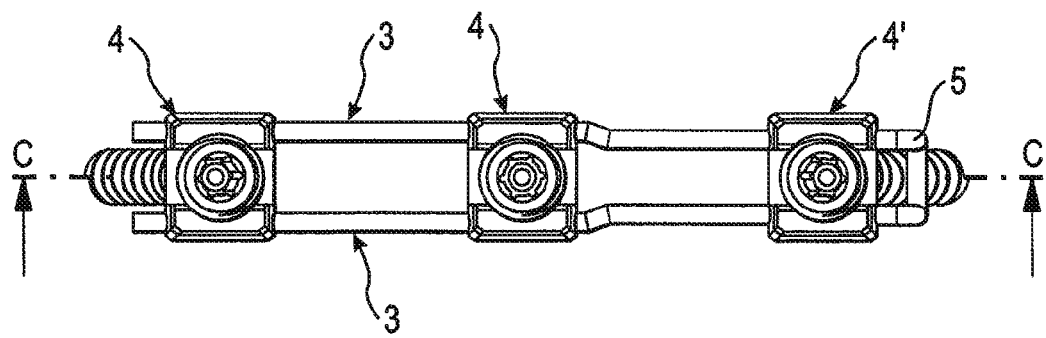
FIG. 9 shows a top view of the stabilization device of FIG. 6.
Figure 10:
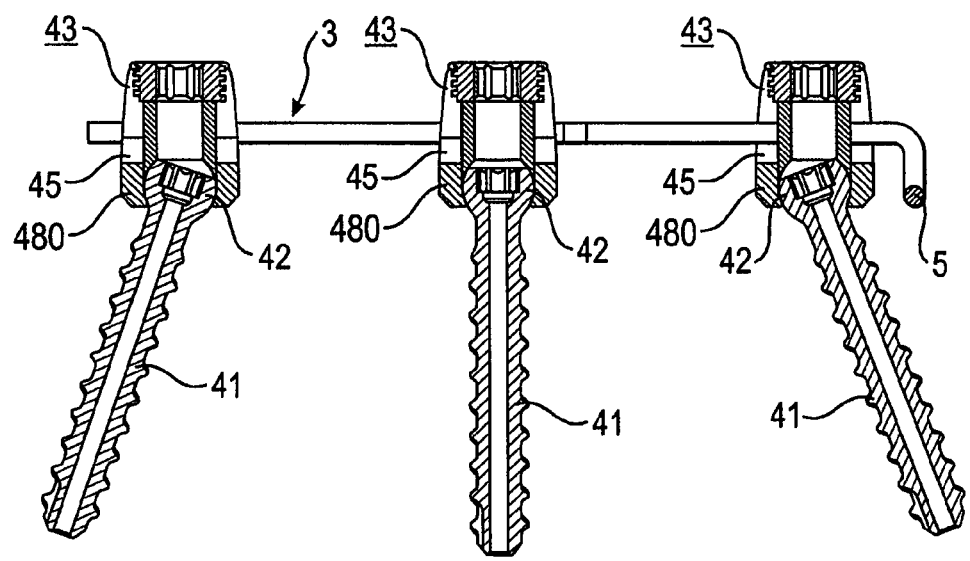
FIG. 10 shows a sectional view along C-C of FIG. 9.

As can be seen in particular in FIG. 5 the receiving part 43 includes a substantially U-shaped recess 45 extending from the first end 43a in the direction of the second end 43b. By means of the U-shaped recess two free legs 46a, 46b are formed which form together with the bottom of the recess a channel for accommodating the flexible rod 2.

In the wall of each of the free legs 46a, 46b bores 47a, 47b are provided and which form guides for the connection rods. The bores 47a, 47b extend through the free legs 46a, 46 so that the connection rods 3 can be guided through the bores from one side of the receiving part and exit through the other side. The size of the bores is such that the diameter is slightly larger than the outer diameter of the connection rods 3 to allow a sliding movement of the connection rods 3 within the bores 47a, 47b.

Figure 2:
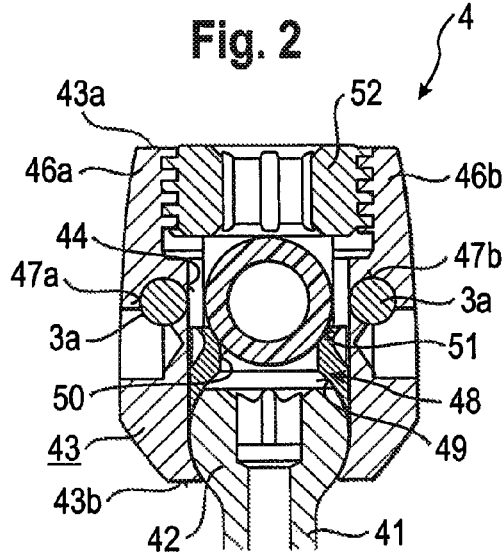
FIG. 2 shows an enlarged sectional view along line A-A in FIG. 1.

In the embodiment shown in FIG. 2 the bores 47a, 47b are located fully within the free legs 46a and 46b and form through holes. The location of the through holes 47a, 47b is such that the bore axis is in one plane with the axis of the flexible rod 2 when the flexible rod 2 is inserted.

The polyaxial bone screw further includes a pressure element 48 which is substantially cylindrical so as to be movable in the bore 44 and which has on its side facing the head 42 a spherical recess 49 to encompass a portion of the head to distribute the pressure onto the head 42. It further includes a coaxial bore 50 to allow access to the head 42. On its side opposite to the spherical recess the pressure element 48 has a cylinder segment-shaped recess 51 which is sized such that the flexible rod 2 can be inserted and guided therein. In the embodiment shown in FIGS. 2 and 3 the cylinder segment-shaped recess 51 is sized such that the flexible rod projects above the pressure element.

The bone anchoring element further includes a fixation screw 52 which engages with an inner thread of the free legs 46a, 46b. The fixation screw 52 serves for pressing onto the flexible rod 2 in the receiving part and therefore indirectly pressing onto the pressure element 48 for exerting pressure onto the head 42 to lock the angular position of the screw element with respect to the receiving part.

Figure 3:
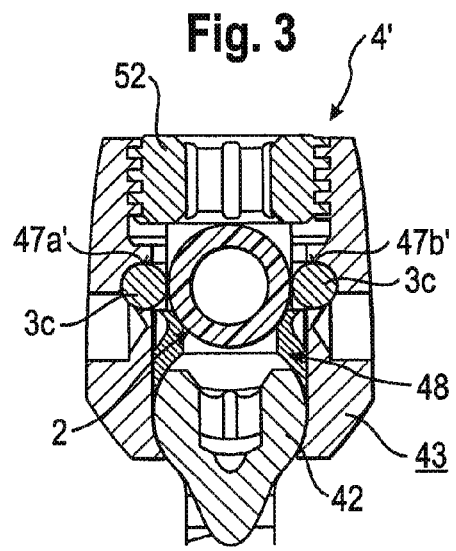
FIG. 3 shows an enlarged sectional view along line B-B in FIG. 1.
Figure 4:
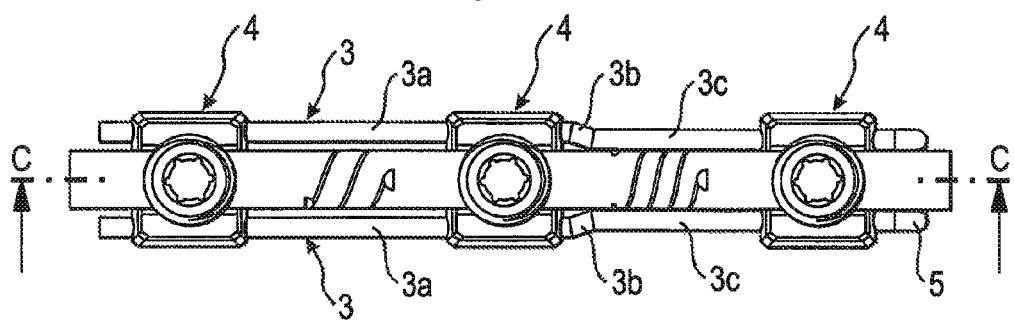
FIG. 4 shows a top view of the stabilization device of FIG. 1.

FIG. 3 shows a bone anchoring element 4' which is a modification of the bone anchoring element which is suitable for accommodating the portion 3c of the connection rods shown in FIG. 4. It differs from the bone anchoring element according to FIG. 2 in the construction of the bores 47a', 47W. All other elements of the bone anchoring element are the same as those of the bone anchoring element of FIG. 2 and the description thereof will not be repeated. The bores 47a', 47b' have a semi-circular cross section. The bores are open to the channel which accommodates the flexible rod 2. The connection rods 3 are secured from inside the receiving part by the flexible rod 2 against falling out from the bores 47a', 47b'. With this embodiment, it is possible to arrange the connection rods 3 more closely to the flexible rod 2 and the connection rods can be put in place through the U-shaped channel. As particularly shown in FIGS. 1 and 4, with this construction it is possible to span several motion segments of the spinal column with different distances of the flexible rod 2 and the connection rods 3 from each other.

Although the first embodiment shows that the connection rods 3 can be connected with each other with a integrally formed bracket 5, other possibilities are possible. For example, the connection rods can be mechanically connected at one or at both ends with a connection which is applied after the rods have been introduced into the receiving parts. They must not necessarily be connected, but can be single rods. To avoid that the single rods escape from the receiving parts in the course of their sliding movement, one end of the rods 3 can have a larger diameter which prevents sliding through the guides.

Although the connection rods are shown as cylindrical rods, the cross section of the connection rods may be non-circular, for example oval-shaped, polygon-shaped or otherwise shaped.

Although the outer shape along the rod axis is shown to have a bent portion 3b in FIG. 4, the connection rods can be straight.

With the bone anchoring element shown in FIG. 2, the connection rods are secured within the bores 47a, 47b against escaping. In specific clinical applications it may be possible to use a stabilizing device without the flexible rod.

The bracket 5 shown in FIG. 1 not only serves for connection of the connection rods 3 but also forms a stop for the sliding movement of the connection rods 3. It is also possible to provide a stop at the opposite end at a distance from the anchoring element 4 so that the connection rods 3 are still fully movable.

The guides and/or the connection rods can be provided with materials and/or devices for facilitating sliding of the connection rods 3. Such materials and/or devices can be, for example, coating, sliding guides or sliding bearings.

FIGS. 6 to 10 show a second embodiment of the stabilization device which differs from the first embodiment shown in FIGS. 1 to 5 only by the pressure element 480 compared to the pressure element 48. The pressure element 480 which allows to omit the flexible rod 2 and to provide stabilization only via the connection rods 3. All other elements and parts are identical to the first embodiment and the description thereof will not be repeated.

The pressure element 480 has instead of the cylinder segment-shaped recess 51 a cylindrical portion 481 which extends coaxially to the main portion of the pressure element and has a diameter which is smaller than the main portion. The length of the cylindrical portion 481 is such that the pressure element extends up to the fixation screw 52 so that the fixation screw 52 can press the pressure element 480 downwards when it is tightened. This embodiment is particularly suitable for applications where a flexible rod is not necessary. If the stabilization device is used without a flexible rod a shown in FIGS. 6 to 10, the pressure element 480 can be used instead of the pressure element 48 while all other parts of the first embodiment remaining the same. Hence, the construction of the bone anchoring element with respect to the bores 47a, 47b or 47a', 47b' remains the same.

Figure 11:
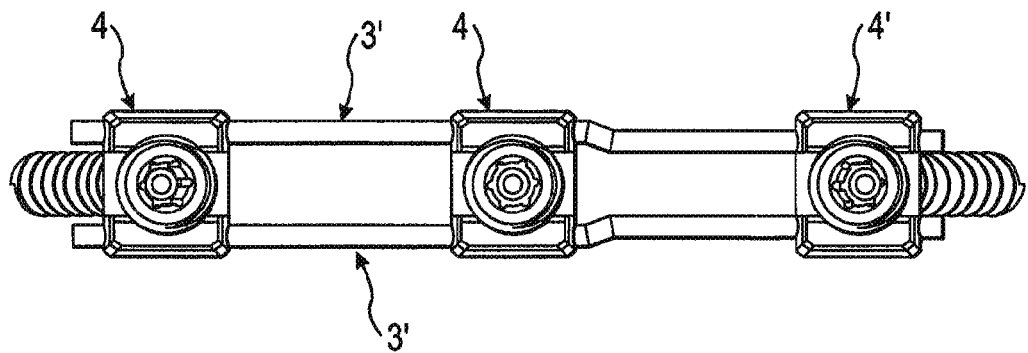
FIG. 11 shows a third embodiment of the stabilization device in a top view.
Figure 12:
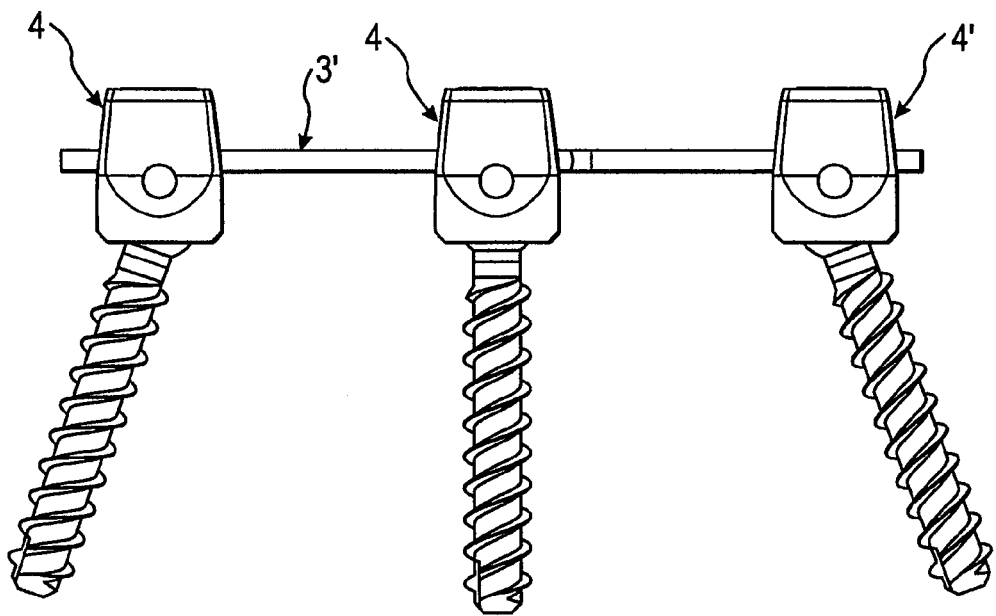
FIG. 12 shows a side view of the stabilization device of FIG. 11.
Figure 15:
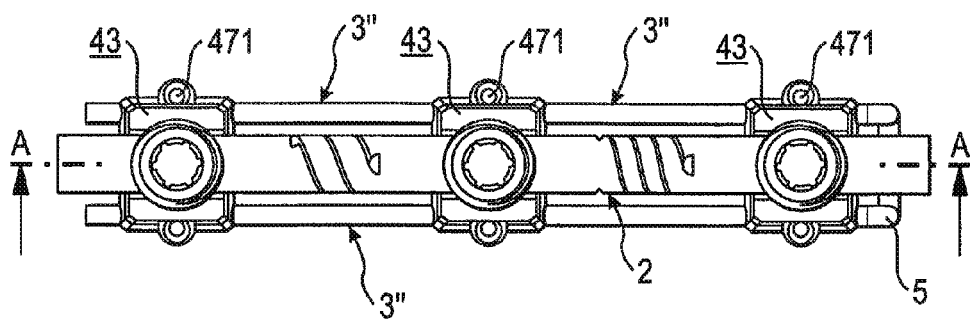
FIG. 15 shows a top view of the stabilization device of FIG. 13.
Figure 16:
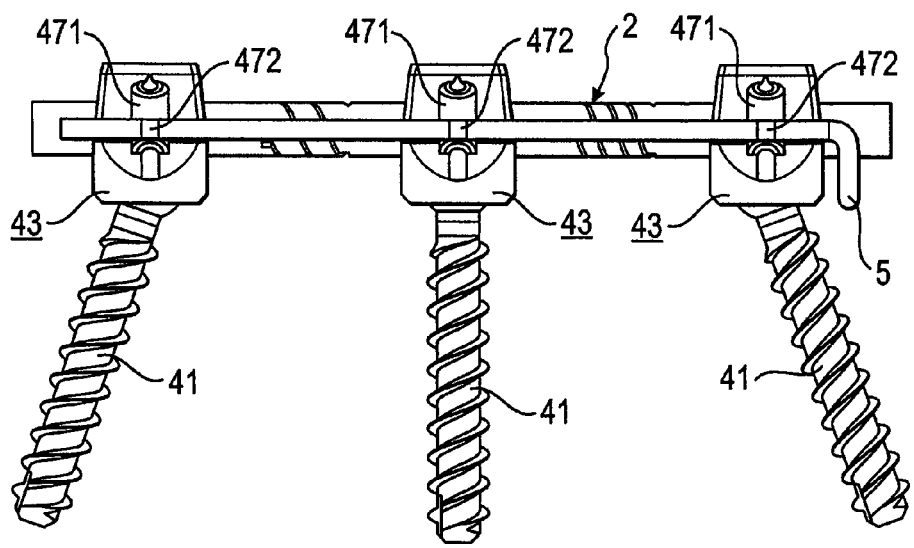
FIG. 16 shows a side view of the stabilization device of FIG. 15.
Figure 17:
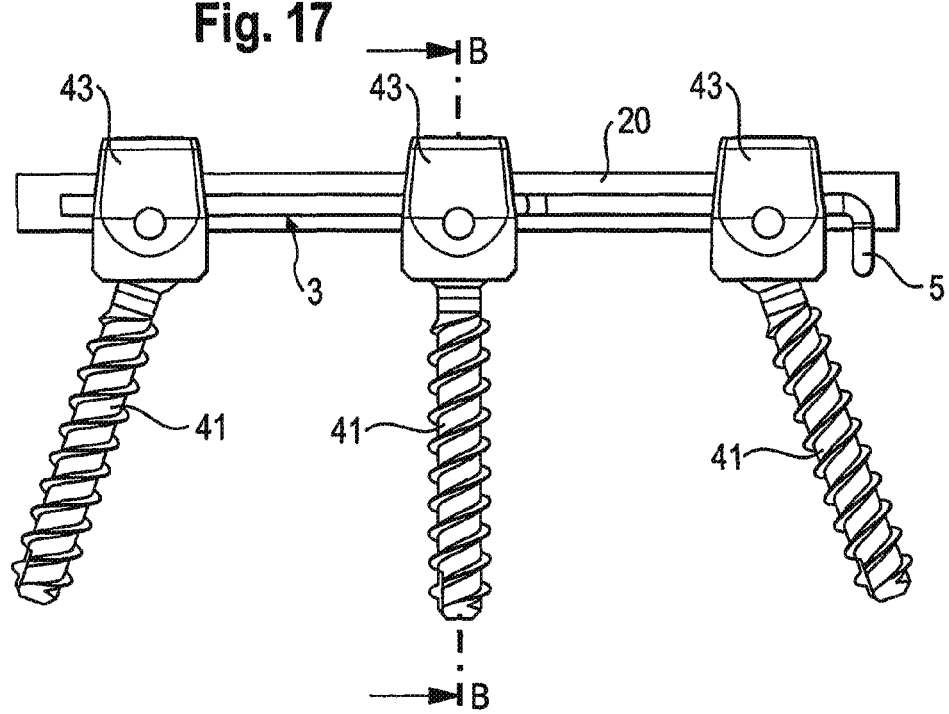
FIG. 17 shows a fifth embodiment of the stabilization device in a side view.

FIGS. 11 and 12 show a third embodiment of the stabilization device which differs from the second embodiment according to FIGS. 6 to 10 only in that the bracket 5 connecting the rods 3 is omitted. In such a case, it is advantageous to provide stops at both ends of the connection rods to allow a free but limited movement of the connecting rods in the receiving parts.

FIGS. 13 to 16 show a fourth embodiment of the stabilization device. In this embodiment a flexible rod 2 and fully straight connection rods 3 are used which are connected by the bracket 5. In this case, the assembly of the connection rods 3 can be introduced in the receiving parts simultaneously by gripping the bracket.

The bone anchoring element 400 of the fourth embodiment differs from the bone anchoring element 4 described in connection with the first embodiment by the location and design of the guides for guiding the connection rods 3. The free legs 46a, 46b have recesses 470a, 470b which are at the outer surface and are open to the outside of the receiving part. The cross section of the recesses 470a, 470b is substantially U-shaped and the size is such that the connection rods 3 can slide therein. To prevent escaping of the rods 3, the free legs 46a, 46b have a support structure 471 supporting a closure element 472, for example a closure bar, which closes the recess 470a, 470b respectively. The recesses 470a, 470b are located at the same height as the bores 47a, 47b of the first embodiment.

All other portions of the bone anchoring element 400 are identical to those of the first embodiment. It shall be noted that the bone anchoring element 400 can also be provided with a pressure element 480 described before when the use of a flexible rod 2 is not necessary.

Figure 18:
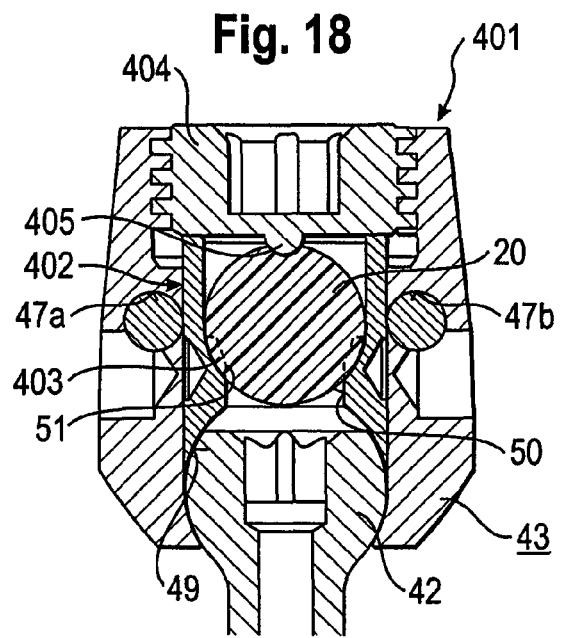
FIG. 18 shows an enlarged sectional view along line B-B of FIG. 17.
Figure 19:
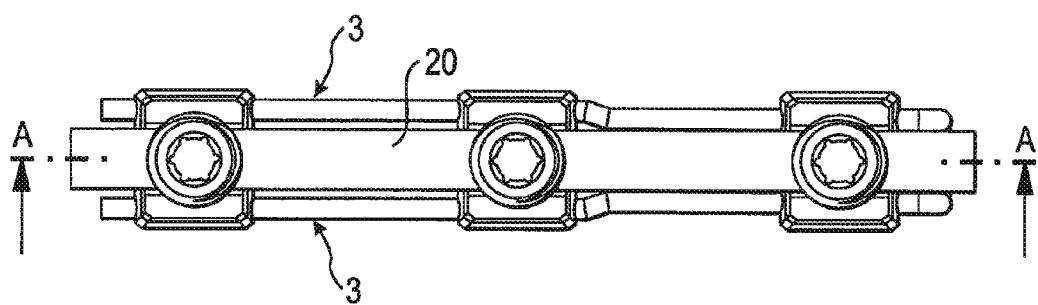
FIG. 19 shows a top view of the fifth embodiment of the stabilization device.
Figure 20:
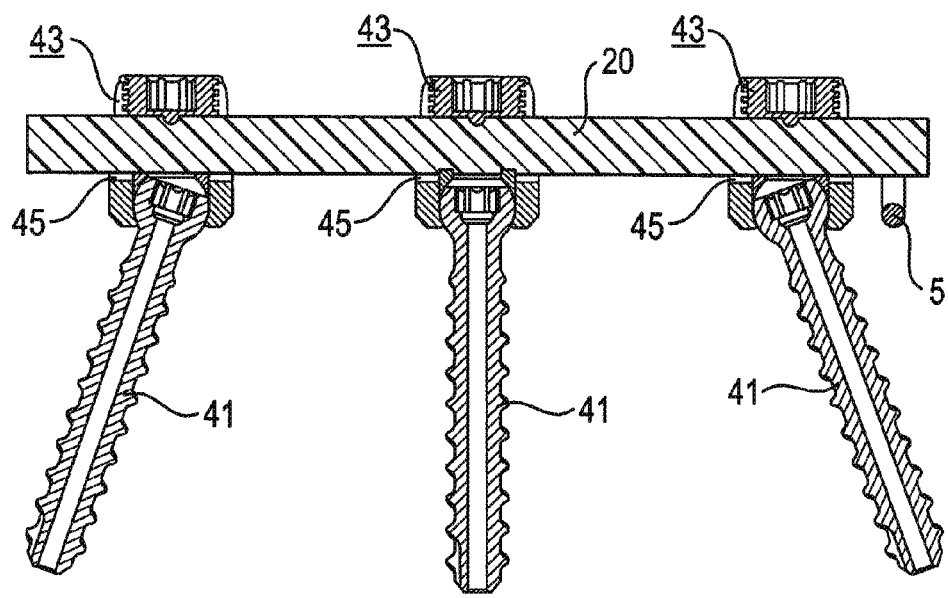
FIG. 20 shows a sectional view of the stabilization device of FIG. 19 along line A-A.

The stabilization device of a fifth embodiment according to FIGS. 17 to 20 has instead of the flexible rod 2 which is a hollow tube with a flexible section, a flexible rod 20 which is made of a flexible plastic material such as an elastomer, for example polyurethane, polycarbonateurethane (PCU) or polysiloxane. The flexible rod 20 exhibits axial flexibility under the action of axial extension or compression. The bone anchoring element 401 is adapted to clamp the flexible rod 20 as can be seen in FIG. 18. The bone anchoring element 401 includes bores 47a, 47b in the wall of the legs as described with respect to the first embodiment and differs from the bone anchoring element of the first embodiment by the shape of the pressure element 402 and the fixation element 404. The pressure element 402 extends above the surface of the flexible rod 20 when the flexible rod 20 is inserted. On the bottom of the recess 51 projections 403 are formed which engage in the surface of the flexible rod 20. The fixation element 404 is a fixation screw as in the first embodiment. However, it has a projection 405 on its lower side facing the flexible rod 20 which engages in the surface structure of the flexible rod 20. By means of this construction the flexible rod 20 is clamped between the pressure element and the fixation screw without blocking the head 42 in the receiving part. The head 42 is locked in its angular position by tightening the fixation screw 404 so that the pressure element presses onto the head.

Although various embodiments have been described in detail the invention is not limited thereto. Single elements of each embodiment can be combined with the other embodiment. In particular, the guides for the connection rods 3 can be varied between the embodiments described. Although specific designs of polyaxial bone screws are described, other designs can also be used, for example polyaxial screws with two part locking elements, polyaxial screws wherein the screw element is loaded into the receiving part from the top or from the bottom, polyaxial screws with various shapes of pressure elements to lock the angular position of the screw element with respect to the receiving part.

Although the embodiments show only polyaxial screws as bone anchoring elements, it is conceivable to provide the guides for the connection rods also in the receiving parts of monoaxial bone screws. However, a dynamic stabilization usually requires the use of polyaxial bone anchoring elements.

In use, first, at least two polyaxial bone anchoring elements are anchored in adjacent vertebral bodies or bone parts. Thereafter, the connection rods are inserted into the guides of the polyaxial bone anchoring elements for aligning the receiving parts with respect to each other in an axial direction. If bone anchoring elements are used which have guides for the connection rods in the form of recesses instead of the through holes the connection rods can be clipped into the recesses by inserting them in the U-shaped channel. This facilitates the step of connecting the bone anchoring elements. Then, the flexible rod is inserted. After insertion of the flexible rod the position and the distance of the bone anchoring elements from each other is adjusted. Finally the flexible rod is fixed by tightening the fixation element. Alternatively, the flexible rod can first be inserted into the U-shaped channels of the bone anchoring elements before guiding the connection rods through the respective guides.

During movements of the motion segments of the spinal column the connection rods 3 can slide within the guides. The connection rods provide resistance against torsional and/or shearing and/or bending forces acting on the stabilization device.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring element comprising:
   an anchoring section for anchoring to a bone;
   a receiving part pivotably connected to the anchoring section, the receiving part comprising two legs defining a generally U-shaped channel extending from free ends of the legs to second ends of the legs that join to define a seat, the seat being configured to receive a stabilization rod along a longitudinal axis of the channel, wherein each leg has a first side and a second side opposite to the first side along the longitudinal axis, and wherein at least a portion of each leg has a thread; and a threaded locking element configured to engage the threads of the legs;

wherein each leg has a substantially straight opening generally oriented along the longitudinal axis and extending through the leg for guiding a connection rod from the first side of the leg to the second side of the leg;

wherein each of the openings is located in a corresponding leg at a location along the leg from the seat to the free end of the leg, and has a bottom that is positioned closer to an end of the receiving part with the free ends of the legs than a bottom of the seat is positioned to the end of the receiving part with the free ends of the legs; and wherein the bone anchoring element is adjustable from a first position where the anchoring section and the receiving part are pivotable relative to one another to a second position where an angular orientation between the anchoring section and the receiving part is locked, and wherein a profile of each of the openings at the first side and at the second side of each corresponding leg to the outside of the bone anchoring element is the same between the first position and the second position.

2. The bone anchoring element of claim 1, wherein the openings are configured as through-holes extending completely through the legs generally in the direction of the longitudinal axis.

3. The bone anchoring element of claim 1, further comprising a securing structure configured to prevent removal of an inserted connection rod from each respective opening.

4. The bone anchoring element of claim 1, wherein the openings are open to the channel.

5. The bone anchoring element of claim 1, wherein the openings are open to an exterior of the receiving part.

6. The bone anchoring element of claim 1, wherein the openings are provided on an outer side of the legs and are integrally formed in the legs.

7. The bone anchoring element of claim 1, wherein the openings are provided on a separate part mounted on an outer side of the legs.

8. The bone anchoring element of claim 1, wherein the openings are smaller than an opening defined by the free ends of the legs of the receiving part.

9. The bone anchoring element of claim 1, wherein the anchoring section and the receiving part form a polyaxial bone screw.

10. The bone anchoring element of claim 1, wherein the opening of each leg has at least a portion with a constant cross-section that extends parallel to the longitudinal axis through the leg.

11. The bone anchoring element of claim 1, wherein each of the openings has at least a portion with a closed cross-section.

12. A stabilization system for bones or a spinal column comprising:

a stabilization rod comprising a flexible section;

two connection rods that are less flexible than the flexible section of the stabilization rod; and at least two bone anchoring elements, each bone anchoring element comprising:

an anchoring section for anchoring to a bone; and a receiving part connected to the anchoring section, the receiving part comprising two legs defining a generally U-shaped channel extending from free ends of the legs to second ends of the legs that join to define a seat, the seat being configured to receive the stabilization rod along a longitudinal axis of the channel, wherein each leg has a first side, a second side opposite to the first side along the longitudinal axis, and an opening generally oriented along the longitudinal axis and extending through the leg from the first side to the second side;

wherein the stabilization rod is configured to be received in the channels of the bone anchoring elements to connect the bone anchoring elements; and wherein each connection rod is configured to be guided through the opening of a corresponding one of the legs of each of the bone anchoring elements, such that when the stabilization rod and the connection rods are received in the bone anchoring elements, the flexible section of the stabilization rod is positioned between the connection rods.

13. The stabilization system of claim 12, wherein the connection rods are connectable to each other at one end.

14. The stabilization system of claim 12, wherein each bone anchoring element further comprises a locking element configured to engage the legs, the locking element being moveable between an unlocked position wherein an inserted stabilization rod is freely movable in the channel and a locked position wherein an inserted stabilization rod is fixed in the channel, and wherein the connection rods are freely moveable in the openings in both the unlocked and the locked positions.

15. The stabilization system of claim 12, wherein each of the openings is located in a corresponding leg at a location along the leg from the seat to the free end of the leg, and has a bottom that is positioned closer to the free end of the leg than a bottom of the seat.

16. The stabilization system of claim 12, wherein a diameter of each of the connection rods is smaller than a diameter of the stabilization rod.

17. The stabilization system of claim 12, wherein the at least two bone anchoring devices comprise polyaxial bone screws, and wherein the connection rods align the receiving parts of the polyaxial bone screws when the connection rods are guided in the openings of the bone anchoring elements.

18. The stabilization system of claim 12, wherein the connection rods are entirely spaced apart in the bone anchoring elements.

19. A method of attaching a stabilization device to bone or vertebra, the stabilization device comprising a stabilization rod comprising a flexible section, two connection rods that are less flexible than the flexible section of the stabilization rod, and at least two bone anchoring elements, each bone anchoring element comprising an anchoring section for anchoring to a bone and a receiving part connected to the anchoring section, the receiving part comprising two legs defining a generally U-shaped channel extending from free ends of the legs to second ends of the legs, wherein each leg has a first side, a second side opposite to the first side along a longitudinal axis of the channel, and an opening generally oriented along the longitudinal axis and extending through the leg from the first side to the second side, the method comprising:

anchoring the anchoring sections of the bone anchoring elements to bone or vertebra;

inserting the stabilization rod in the channel of each receiving part; and guiding the connection rods through corresponding ones of the openings in the legs of each receiving part, such that the flexible section of the stabilization rod is positioned between the connection rods.

20. The method of claim 19, wherein the stabilization rod is inserted in the channel of each receiving part before guiding the connection rods through the openings of the legs of each receiving part.

21. The method of claim 19, wherein the connection rods are guided through the openings of the legs of each receiving part before inserting the stabilization rod in the channel of each receiving part.

22. The method of claim 19, further comprising moving a locking element of each bone anchoring element from an unlocked position wherein the stabilization rod is freely movable in the channel of each receiving part, to a locked position wherein the stabilization rod is fixed in the channel of each receiving part, and wherein the connection rods are freely moveable in the openings in both the unlocked and the locked positions.

23. A bone anchoring element comprising:
an anchoring section for anchoring to a bone;
a receiving part connected to the anchoring section, the receiving part comprising two legs defining a generally U-shaped channel extending from free ends of the legs to second ends of the legs that join to define a seat, the seat being configured to receive a stabilization rod along a longitudinal axis of the channel, wherein each leg has a first side and a second side opposite to the first side along the longitudinal axis, and wherein at least a portion of each leg has a thread; and
a threaded locking element configured to engage the threads of the legs;
wherein each leg has an opening generally oriented along the longitudinal axis and extending through the leg for guiding a connection rod from the first side of the leg to the second side of the leg; and
wherein each of the openings is located in a corresponding leg at a location along the leg from the seat to the free end of the leg, is open to the channel and to an outer wall of the receiving part at the first side and the second side of the leg, and has a bottom that is positioned closer to an end of the receiving part with the free ends of the legs than a bottom of the seat is positioned to the end of the receiving part with the free ends of the legs.

24. The bone anchoring element of claim 23, wherein the openings are configured as through-holes extending completely through the legs generally in the direction of the longitudinal axis.

25. The bone anchoring element of claim 23, further comprising a securing structure configured to prevent removal of an inserted connection rod from each respective opening.

26. The bone anchoring element of claim 23, wherein the openings are open to an exterior of the receiving part.

27. The bone anchoring element of claim 23, wherein the openings are smaller than an opening defined by the free ends of the legs of the receiving part.

28. The bone anchoring element of claim 23, wherein the anchoring section is pivotably connected to the receiving part.

29. The bone anchoring element of claim 28, wherein the anchoring section and the receiving part form a polyaxial bone screw.

30. A bone anchoring element comprising:
an anchoring section for anchoring to a bone;
a receiving part connected to the anchoring section, the receiving part comprising two legs defining a generally U-shaped channel extending from free ends of the legs to second ends of the legs that join to define a seat, the seat being configured to receive a stabilization rod along a longitudinal axis of the channel, wherein each leg has a first side and a second side opposite to the first side along the longitudinal axis, and wherein at least a portion of each leg has a thread; and
a threaded locking element configured to engage the threads of the legs;
wherein each leg has a substantially straight opening generally oriented along the longitudinal axis and extending through the leg for guiding a connection rod from the first side of the leg to the second side of the leg; and
wherein each of the openings is located in a corresponding leg at a location along the leg from the seat to the free end of the leg, and opens laterally on a side of the leg opposite a side facing the channel in a direction perpendicular to the longitudinal axis of the channel.

31. The bone anchoring element of claim 30, wherein the openings are provided on a separate part mounted on an outer side of the legs.

32. The bone anchoring element of claim 30, wherein the openings are configured as through-holes extending completely through the legs generally in the direction of the longitudinal axis.

33. The bone anchoring element of claim 30, further comprising a securing structure configured to prevent removal of an inserted connection rod from each respective opening.

34. The bone anchoring element of claim 30, wherein the openings are smaller than an opening defined by the free ends of the legs of the receiving part.

35. The bone anchoring element of claim 30, wherein the anchoring section is pivotably connected to the receiving part.

36. The bone anchoring element of claim 35, wherein the anchoring section and the receiving part form a polyaxial bone screw.

* * * * *